(12) United States Patent
Hara et al.

(10) Patent No.: US 10,161,889 B2
(45) Date of Patent: Dec. 25, 2018

(54) X-RAY FLUORESCENCE SPECTROMETER

(71) Applicant: Rigaku Corporation, Tokyo (JP)

(72) Inventors: Shinya Hara, Takatsuki (JP); Takashi Matsuo, Takatsuki (JP); Yasujiro Yamada, Takatsuki (JP); Hisashi Honma, Takatsuki (JP); Yoshiyuki Kataoka, Takatsuki (JP)

(73) Assignee: Rigaku Corporation, Akishima-shi, Tokyo (JP)

( * ) Notice: Subject to any disclaimer, the term of this patent is extended or adjusted under 35 U.S.C. 154(b) by 0 days.

(21) Appl. No.: 15/901,244

(22) Filed: Feb. 21, 2018

(65) Prior Publication Data

US 2018/0180563 A1 Jun. 28, 2018

Related U.S. Application Data

(63) Continuation of application No. PCT/JP2016/075034, filed on Aug. 26, 2016.

(30) Foreign Application Priority Data

Aug. 28, 2015 (JP) ................................. 2015-169543

(51) Int. Cl.
*G01N 23/223* (2006.01)
*G01N 23/207* (2018.01)
*G01N 23/2209* (2018.01)

(52) U.S. Cl.
CPC .......... *G01N 23/223* (2013.01); *G01N 23/207* (2013.01); *G01N 23/2076* (2013.01); *G01N 23/2209* (2018.02); *G01N 2223/076* (2013.01)

(58) Field of Classification Search
CPC ........... G01N 2223/076; G01N 23/207; G01N 23/2209; G01N 23/223; G01N 23/2076; G01N 2223/303; G01N 2223/3037
See application file for complete search history.

(56) References Cited

U.S. PATENT DOCUMENTS 5,062,127 A 10/1991 Sayama et al.
6,041,096 A 3/2000 Doi et al.
(Continued)

FOREIGN PATENT DOCUMENTS

CN 1952652 A 4/2007
CN 102187208 A 9/2011
(Continued)

OTHER PUBLICATIONS

Notification Concerning Documents Transmitted dated Sep. 5, 2017, issued by the International Bureau in International Application No. PCT/JP2016/075033.
(Continued)

*Primary Examiner* — Glen Kao
*Assistant Examiner* — Chih-Cheng Kao
(74) *Attorney, Agent, or Firm* — Sughrue Mion, PLLC (57) ABSTRACT

A quantitative analysis condition setting unit (13) included in a sequential X-ray fluorescence spectrometer according to the present invention: performs qualitative analyses of a plurality of standard samples (14); sets, on the basis of the qualitative analysis results, a peak measurement angle of each measurement line for analytical samples (1) in quantitative analysis conditions; and obtains a single virtual profile by synthesizing peak profiles of the plurality of standard samples (14) subjected to the qualitative analyses and sets, on the basis of the virtual profile and a preset half value width of the peak profile, background measurement angles of each measurement line for the analytical samples (1) in the quantitative analysis conditions.

5 Claims, 7 Drawing Sheets

(56) References Cited

U.S. PATENT DOCUMENTS

| | | | |
|---|---|---|---|
| 6,668,038 | B2 | 12/2003 | Kataoka et al. |
| 6,845,147 | B2 | 1/2005 | Elam et al. |
| 7,450,685 | B2 | 11/2008 | Kataoka et al. |
| 8,433,035 | B2 | 4/2013 | Watanabe et al. |
| 2004/0066886 | A1 | 4/2004 | Elam et al. |
| 2007/0086567 | A1* | 4/2007 | Kataoka ............... G01N 23/223 |
| | | | 378/45 |
| 2011/0243301 | A1 | 10/2011 | Watanabe et al. |
| 2016/0258890 | A1 | 9/2016 | Zarkadas et al. |
| 2017/0184519 | A1* | 6/2017 | Sako .................... G01N 23/223 |

FOREIGN PATENT DOCUMENTS

| | | |
|---|---|---|
| EP | 0 400 396 A2 | 12/1990 |
| JP | 2000-310602 A | 11/2000 |
| JP | 2002-340822 A | 11/2002 |
| JP | 2004-212406 A | 7/2004 |
| JP | 3567177 B2 | 9/2004 |
| JP | 2013-205080 A | 10/2013 |
| WO | 03/107037 A2 | 12/2003 |

OTHER PUBLICATIONS

Extended European Search Report dated Dec. 5, 2017, issued by the European Patent Office in counterpart European Application No. 16841733.5.
Communication dated Jan. 22, 2018, issued by the State Intellectual Property Office of the People's Republic of China in counterpart Chinese Application No. 201680006771.9.
Written Opinion of the International Searching Authority for PCT/JP2016/075033 dated Nov. 1, 2016.
International Search Report for PCT/JP2016/075033 dated Nov. 1, 2016.
Communication dated Sep. 12, 2017 from the Japanese Patent Office in counterpart Application No. 2017-537853.
Translation of International Preliminary Report on Patentability dated Mar. 15, 2018, in counterpart International Application No. PCT/JP2016/075034.
International Search Report for PCT/JP2016/075034, dated Nov. 1, 2016 (PCT/ISA/237).
Communication dated Aug. 31, 2018 from the State Intellectual Property Office of the P.R.C. in counterpart application No. 201680049794.8.

* cited by examiner

X-RAY FLUORESCENCE SPECTROMETER

CROSS REFERENCE TO THE RELATED APPLICATION

This application is a continuation application, under 35 U.S.C. § 111(a), of international application No. PCT/JP2016/075034, filed Aug. 26, 2016, which claims priority to Japanese patent application No. 2015-169543, filed Aug. 28, 2015, the entire disclosure of which is herein incorporated by reference as a part of this application.

BACKGROUND OF THE INVENTION

Field of the Invention

The present invention relates to a sequential X-ray fluorescence spectrometer which irradiates a sample with primary X-rays and measures intensities of generated secondary X-rays.

Description of Related Art

There has conventionally been a sequential X-ray fluorescence spectrometer that irradiates a sample with primary X-rays, measures intensities of secondary X-rays such as fluorescent X-rays generated from the sample, and performs a quantitative analysis of, e.g., contents of elements in the sample on the basis of the measured intensities. In such a spectrometer, standard samples corresponding to analytical samples are provided. Measurement lines for the analytical samples, the sample constituting elements and their contents (chemical analytical values) of each standard sample are preset as quantitative analysis conditions. Calibration curves are created by measuring the standard samples. And then quantitative analyses of the analytical samples are performed.

Regarding setting of the quantitative analysis conditions, there has been an X-ray fluorescence spectrometer including a sample type storage unit, a semi-quantitative analysis unit, a type determining unit, and a quantitative analysis unit, wherein determination of a type of a sample based on a semi-quantitative analysis result and the quantitative analysis under analysis conditions appropriate for the determined type are automatically performed (see Patent Document 1). Here, appropriate analysis conditions for respective types to be prestored in the sample type storage unit may include a peak measurement angle and background measurement angles of each measurement line to be measured by a detecting unit. In this case, for example, an operator needs to perform a qualitative analysis of representative one of a plurality of standard samples corresponding to each sample type, and to determine the peak measurement angle and the background measurement angles of each measurement line from the obtained peak profile of the corresponding measurement line on the basis of the experience of the operator. The measurement angles are each expressed by a spectroscopic angle (a so-called angle 2θ which is twice as large as an incident angle) in a spectroscopic device.

RELATED DOCUMENT

Patent Document

[Patent Document 1] JP Laid-open Patent Publication No. 2002-340822

However, considering the fact that interfering lines against the measurement line appear differently depending on an individual sample, if the peak measurement angle and the background measurement angles of each measurement line for the analytical samples in the quantitative analysis conditions are set on the basis of the qualitative analysis of only one standard sample, appropriate setting is not necessarily performed. However, if the qualitative analyses are performed on a plurality of standard samples, a long time is taken and it is not easy to appropriately reflect the qualitative analysis results to set the peak measurement angle and the background measurement angles of each measurement line for the analytical samples.

SUMMARY OF THE INVENTION

The present invention has been made in view of the above problems, and an object thereof is to provide a sequential X-ray fluorescence spectrometer in which qualitative analyses of a plurality of standard samples are automatically performed and a peak measurement angle and background measurement angles of each measurement line for the analytical samples are automatically set by appropriately reflecting the qualitative analysis results, so that analyses can be accurately performed.

In order to achieve the aforementioned object, a first aspect according to the present invention is a sequential X-ray fluorescence spectrometer which irradiates a sample with primary X-rays and measures the intensities of generated secondary X-rays, and which includes a plurality of standard samples for creating calibration curves corresponding to analytical samples, and a quantitative analysis condition setting unit configured to preset, as quantitative analysis conditions, with measurement lines for the analytical samples, a half value width of a peak profile of each measurement line, sample constituting elements and their contents of each standard sample.

The quantitative analysis condition setting unit performs qualitative analyses of the plurality of standard samples, and obtains, for each of measurement lines identified in each standard sample, a peak angle obtained through peak search, background angles based on the peak angle and the preset half value width of the peak profile, and a net intensity based on a peak intensity at the peak angle and background intensities at the background angles.

Further, the quantitative analysis condition setting unit sets, for each of the measurement lines, the peak angle of the standard sample at which no interfering line is identified within a predetermined angle range centered on the measurement line and the peak intensity is maximum, as a peak measurement angle of the measurement line for the analytical samples in the quantitative analysis conditions, and further, obtains, for each of the measurement lines, a single virtual profile by synthesizing peak profiles of the plurality of standard samples subjected to the qualitative analyses, and sets the background angle on each of a lower angle side and a higher angle side relative to the measurement line, as a background measurement angle of the measurement line for the analytical samples in the quantitative analysis conditions, the background angles being based on the virtual profile and the preset half value width of the peak profile.

The X-ray fluorescence spectrometer according to the first aspect of the present invention includes the quantitative analysis condition setting unit that performs the qualitative analyses of the plurality of standard samples, that sets the peak angle of the standard sample, at which no interfering line is identified within the predetermined angle range centered on the measurement line and the peak intensity is maximum, as a peak measurement angle of the measurement line for the analytical samples in the quantitative analysis conditions, and that obtains the single virtual profile by synthesizing the peak profiles of the plurality of standard samples subjected to the qualitative analyses, and sets the background angles based on the virtual profile and the preset half value width of the peak profile, as the background measurement angles of the measurement line for the analytical samples in the quantitative analysis conditions. Accordingly, the qualitative analyses of the plurality of standard samples are automatically performed and the peak measurement angle and the background measurement angles of each measurement line for the analytical samples are automatically set by appropriately reflecting the qualitative analysis results, so that accurate analyses can be performed.

A second aspect according to the present invention is a sequential X-ray fluorescence spectrometer which irradiates a sample with primary X-rays and measures the intensities of generated secondary X-rays, and which includes a plurality of standard samples for creating calibration curves corresponding to analytical samples, and a quantitative analysis condition setting unit configured to preset, as quantitative analysis conditions, with measurement lines for the analytical samples, a half value width of a peak profile of each measurement line, sample constituting elements and their contents of each standard sample.

The quantitative analysis condition setting unit performs qualitative analyses of the plurality of standard samples, to obtain, for each of measurement lines identified in each standard sample, a peak angle obtained through peak search, background angles based on the peak angle and the preset half value width of the peak profile, and a net intensity based on a peak intensity at the peak angle and background intensities at the background angles.

Further, the quantitative analysis condition setting unit sets, for each of the measurement lines, the peak angle of the standard sample at which no interfering line is identified within a predetermined angle range centered on the measurement line and the peak intensity is maximum, as a peak measurement angle of the measurement line for the analytical samples in the quantitative analysis conditions, and obtains, for each of the measurement lines, background measurement angle ranges on the basis of the peak profile of the corresponding standard sample and the preset half value width of the peak profile, and sets an angle, which is closest to the measurement line within the background measurement angle range, on each of a lower angle side and a higher angle side relative to the measurement line, as a background measurement angle of the measurement line for the analytical samples in the quantitative analysis conditions, the background measurement angle range being common to the plurality of standard samples subjected to the qualitative analyses.

The X-ray fluorescence spectrometer according to the second aspect of the present invention includes the quantitative analysis condition setting unit that performs the qualitative analyses of the plurality of standard samples, that sets, as the peak measurement angle of the measurement line for the analytical samples in the quantitative analysis conditions, the peak angle of the standard sample at which no interfering line is identified within the predetermined angle range centered on the measurement line and the peak intensity is maximum, and that obtains the background measurement angle ranges on the basis of the peak profile of the corresponding standard sample and the preset half value width of the peak profile and sets, as each background measurement angle of the measurement line for the analytical samples in the quantitative analysis conditions, each angle closest to the measurement line within the background measurement angle range which is common to the plurality of standard samples subjected to the qualitative analyses. Accordingly, as in the spectrometer according to the first aspect, the qualitative analyses of the plurality of standard samples are automatically performed and the peak measurement angle and the background measurement angles of each measurement line for the analytical samples are automatically set by appropriately reflecting the qualitative analysis results, so that accurate analyses can be performed.

In the X-ray fluorescence spectrometer according to the first aspect of the present invention, it is preferable that the quantitative analysis condition setting unit sets, as new background measurement angles of the measurement line for the analytical samples in the quantitative analysis conditions, the background measurement angles by which the background intensity at the peak measurement angle of the measurement line is minimized when, in the virtual profile, the background measurement angles of the measurement line which are set on the lower angle side and the higher angle side relative to the measurement line are alternately brought closer to the measurement line within a predetermined angle range, at a predetermined angle step.

In a case where the peak of the measurement line appears in a region where the intensity of scattered X-rays of continuous X-rays of the primary X-rays is high, or in a skirt of the peak profile of the interfering line having a high intensity, if the set background measurement angles of the measurement line are adopted as they are, the background intensity at the peak measurement angle of the measurement line becomes excessively high and the net intensity of the measurement line becomes negative, so that sufficiently accurate analysis cannot be performed. For this reason, with this preferable feature in the X-ray fluorescence spectrometer according to the first aspect, the background measurement angles of the measurement line for the analytical samples in the quantitative analysis conditions are corrected and set so as to appropriately minimize the background intensity at the peak measurement angle of the measurement line.

In the X-ray fluorescence spectrometer according to the second aspect of the present invention, it is preferable that the quantitative analysis condition setting unit sets, as new background measurement angles of the measurement line for each of the standard samples, the background measurement angles by which the background intensity at the peak measurement angle of the measurement line is minimized when, in the peak profile of the corresponding standard sample, the background measurement angles of the measurement line which are set on the lower angle side and the higher angle side relative to the measurement line are alternately brought closer to the measurement line within a predetermined angle range, at a predetermined angle step, and sets, on each of the lower angle side and the higher angle side relative to the measurement line, as a new background measurement angle of the measurement line for the analytical samples in the quantitative analysis conditions, the background measurement angle of the measurement line which is farthest from the peak measurement angle of the measurement line, among the new background measurement angles of the measurement lines of the plurality of standard samples subjected to the qualitative analyses.

As described above, depending on the state of appearance of the peak of the measurement line, if the set background measurement angles of the measurement line are adopted as they are, the background intensity at the peak measurement angle of the measurement line becomes excessively high and the net intensity of the measurement line becomes negative, so that sufficiently accurate analysis cannot be performed. For this reason, with this preferable feature in the X-ray fluorescence spectrometer according to the second aspect, the background measurement angles of the measurement line for the analytical samples in the quantitative analysis conditions are corrected and set so as to appropriately minimize the background intensity at the peak measurement angle of the measurement line.

In the X-ray fluorescence spectrometer according to the first aspect of the present invention, it is preferable that the quantitative analysis condition setting unit obtains, for each of the measurement lines, a net intensity based on the set background measurement angles of the measurement line for each of the plurality of standard samples subjected to the qualitative analyses, and when, in at least one of the standard samples, the obtained net intensity is negative and the absolute value of the obtained net intensity is greater than a theoretical standard deviation of the net intensity, the quantitative analysis condition setting unit cancels setting of the background measurement angle at which the background intensity is higher in the virtual profile, of the background measurement angles of the measurement line which are set on the lower angle side and the higher angle side relative to the measurement line.

As described above, depending on the state of appearance of the peak of the measurement line, if the set background measurement angles of the measurement line on the lower angle side and the higher angle side relative to the measurement line are adopted as they are, the background intensity at the peak measurement angle of the measurement line becomes excessively high and the net intensity of the measurement line becomes negative, so that sufficiently accurate analysis cannot be performed. For this reason, in such a case, with this preferable feature in the X-ray fluorescence spectrometer according to the first aspect, the background measurement angles of the measurement line for the analytical samples in the quantitative analysis conditions are corrected and set such that, of the set background measurement angles of the measurement line on the lower angle side and the higher angle side relative to the measurement line, only the background measurement angle at which the background intensity is lower in the virtual profile remains.

Any combination of at least two constructions, disclosed in the appended claims and/or the specification and/or the accompanying drawings should be construed as included within the scope of the present invention. In particular, any combination of two or more of the appended claims should be construed as included within the scope of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF EMBODIMENTS

Figure 1:
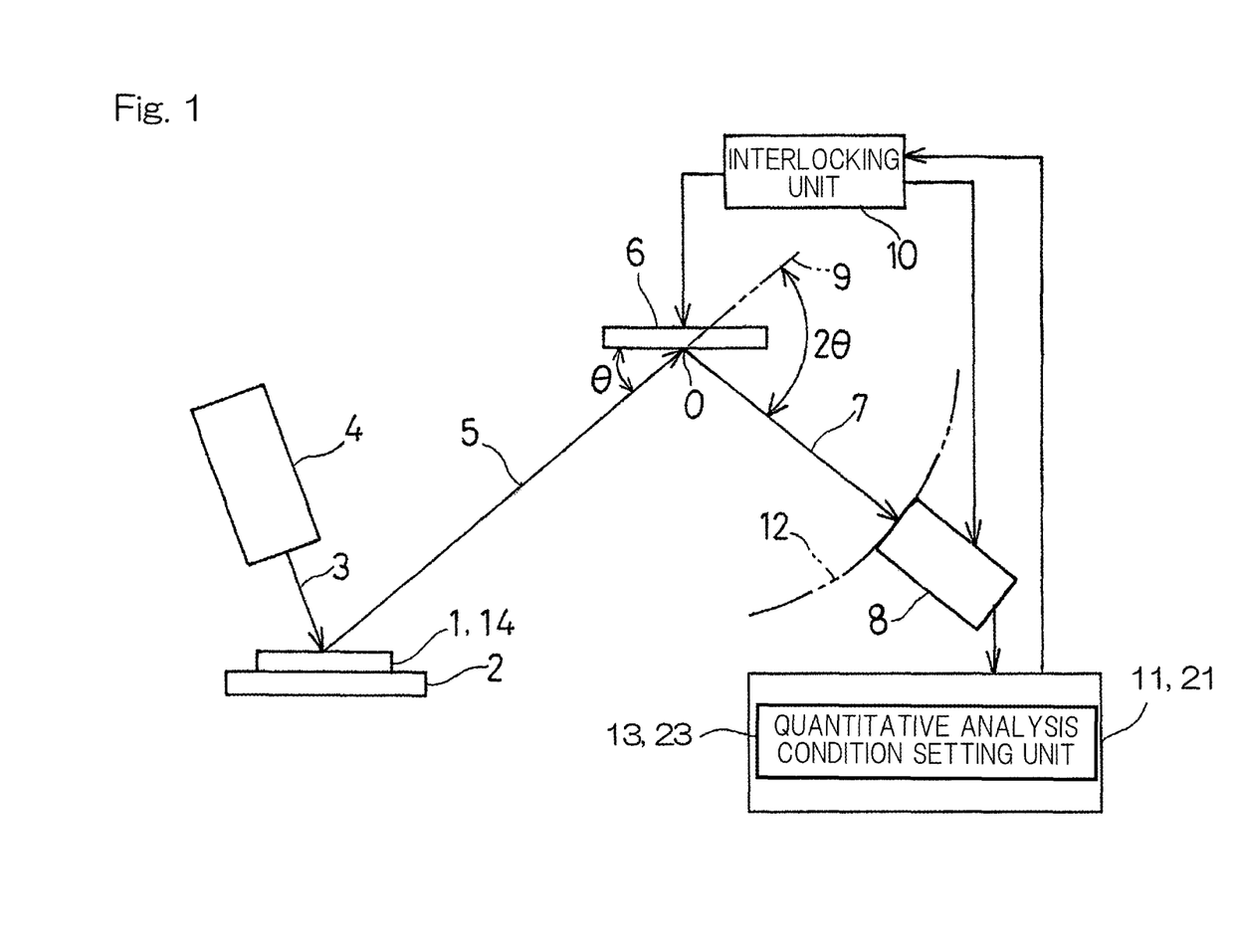
FIG. 1 is a schematic diagram illustrating an X-ray fluorescence spectrometer according to a first or second embodiment of the present invention.

Hereinafter, a spectrometer according to a first embodiment of the present invention will be described with reference to the drawings. As illustrated in FIG. 1, the spectrometer is a sequential X-ray fluorescence spectrometer that irradiates samples 1, 14 with primary X-rays 3, and measures the intensities of generated secondary X-rays 5. The spectrometer includes a sample stage 2 on which the sample 1, 14 is placed, an X-ray source 4 such as an X-ray tube configured to irradiate the sample 1, 14 with the primary X-rays 3, a spectroscopic device 6 which monochromates the secondary X-rays 5 such as fluorescent X-rays generated from the sample 1, 14, and a detector 8 on which secondary X-rays 7 monochromated by the spectroscopic device 6 are incident and which detects the intensity of the secondary X-rays 7. An output from the detector 8 is inputted, through an amplifier, a pulse height analyzer, counting unit, and the like (not illustrated), to a control unit 11 configured to control the entire spectrometer.

The spectrometer is a wavelength dispersive and sequential X-ray fluorescence spectrometer, and includes an interlocking unit 10, i.e., a so-called goniometer, configured to interlock the spectroscopic device 6 with the detector 8 so as to change the wavelengths of the secondary X-rays 7 incident on the detector 8. When the secondary X-rays 5 are incident on the spectroscopic device 6 at a certain incident angle $\theta$, an extended line 9 of the secondary X-rays 5 and the secondary X-rays 7 monochromated (diffracted) by the spectroscopic device 6 form a spectroscopic angle $2\theta$, which is twice the incident angle $\theta$. To cause the secondary X-rays 7, which are monochromated while the spectroscopic angle 20 is changed, to be incident on the detector 8 while changing the wavelengths of the secondary X-rays 7, the interlocking unit 10 rotates the spectroscopic device 6 around an axis O, which passes a center of a surface of the spectroscopic device 6 and is perpendicular to the drawing sheet, and rotates the detector 8 around the axis O and along a circle 12 by an angle of twice the rotation angle of the spectroscopic device 6. The value of the spectroscopic angle 20 (angle 20) is inputted from the interlocking unit 10 to the control unit 11.

The spectrometer includes a plurality of standard samples 14 which are for creating calibration curves corresponding to analytical samples 1 and which have different compositions, and further includes, as a part of the control unit 11, a quantitative analysis condition setting unit 13 configured to preset, as quantitative analysis conditions, with measurement lines for the analytical samples 1, a half value width of a peak profile of each measurement line, sample constituting elements and their contents of each standard sample 14. The analytical sample 1 and the standard sample 14 are collectively referred to as the samples 1, 14.

The quantitative analysis condition setting unit 13 performs qualitative analyses of the plurality of standard samples 14, and obtains, for each of measurement lines identified in each standard sample 14, a peak angle obtained through peak search, background angles based on the peak angle and the preset half value width of the peak profile, and a net intensity based on a peak intensity at the peak angle and background intensities at the background angles.

Here, the qualitative analysis refers to analysis in which a spectrum is obtained by measuring the intensities of the secondary X-rays 5 in a wide wavelength range under a predetermined standard analysis condition, and then, smoothing, peak search, calculation of the net intensities of peaks, and identification and analysis of the peaks are performed. For example, spectra of all the elements F to U are measured by scanning the goniometer 10, and the peaks detected from the measured spectra are identified and analyzed. The peaks include not only the peaks of the measurement lines but also the peaks of the interfering lines. On the other hand, quantitative analysis refers to analysis in which, on the basis of X-ray intensities measured with the goniometer 10 being fixed respectively, the contents of respective elements are determined by using calibration curves corresponding to the analytical samples 1, or by a fundamental parameter procedure using prestored apparatus sensitivity factors.

On the basis of the qualitative analysis results, the quantitative analysis condition setting unit 13 sets, for each of the measurement lines, the peak angle of the standard sample 14 at which no interfering line is identified within a predetermined angle range centered on the measurement line and the peak intensity is maximum, as a peak measurement angle of the measurement line for the analytical samples 1 in the quantitative analysis conditions.

Further, for each of the measurement lines, the quantitative analysis condition setting unit 13 obtains a single virtual profile by synthesizing (e.g., summing up or averaging) peak profiles of the plurality of standard samples 14 subjected to the qualitative analyses, and sets, on each of the lower angle side and the higher angle side relative to the measurement line, the background angle based on the virtual profile and the preset half value width of the peak profile, as a background measurement angle of the measurement line for the analytical samples 1 in the quantitative analysis conditions.

Furthermore, not necessarily in the X-ray fluorescence spectrometer of the present invention, but in the X-ray fluorescence spectrometer according to the first embodiment, the quantitative analysis condition setting unit 13 sets, as new background measurement angles of the measurement line for the analytical samples 1 in the quantitative analysis conditions, the background measurement angles by which the background intensity at the peak measurement angle of the measurement line is minimized when, in the virtual profile, the background measurement angles of the measurement line set on the lower angle side and the higher angle side relative to the measurement line are alternately brought closer to the measurement line within a predetermined angle range, at a predetermined angle step.

Moreover, not necessarily in the X-ray fluorescence spectrometer of the present invention, but in the X-ray fluorescence spectrometer according to the first embodiment, the quantitative analysis condition setting unit 13 obtains, for each of the measurement lines, a net intensity based on the set background measurement angles of the measurement line for each of the plurality of standard samples 14 subjected to the qualitative analyses, and when, in at least one of the standard samples 14, the obtained net intensity is negative and the absolute value of the obtained net intensity is greater than a theoretical standard deviation of the net intensity, the quantitative analysis condition setting unit 13 cancels setting of the background measurement angle at which the background intensity is higher in the virtual profile, of the background measurement angles of the measurement line set on the lower angle side and the higher angle side relative to the measurement line.

Figure 2:
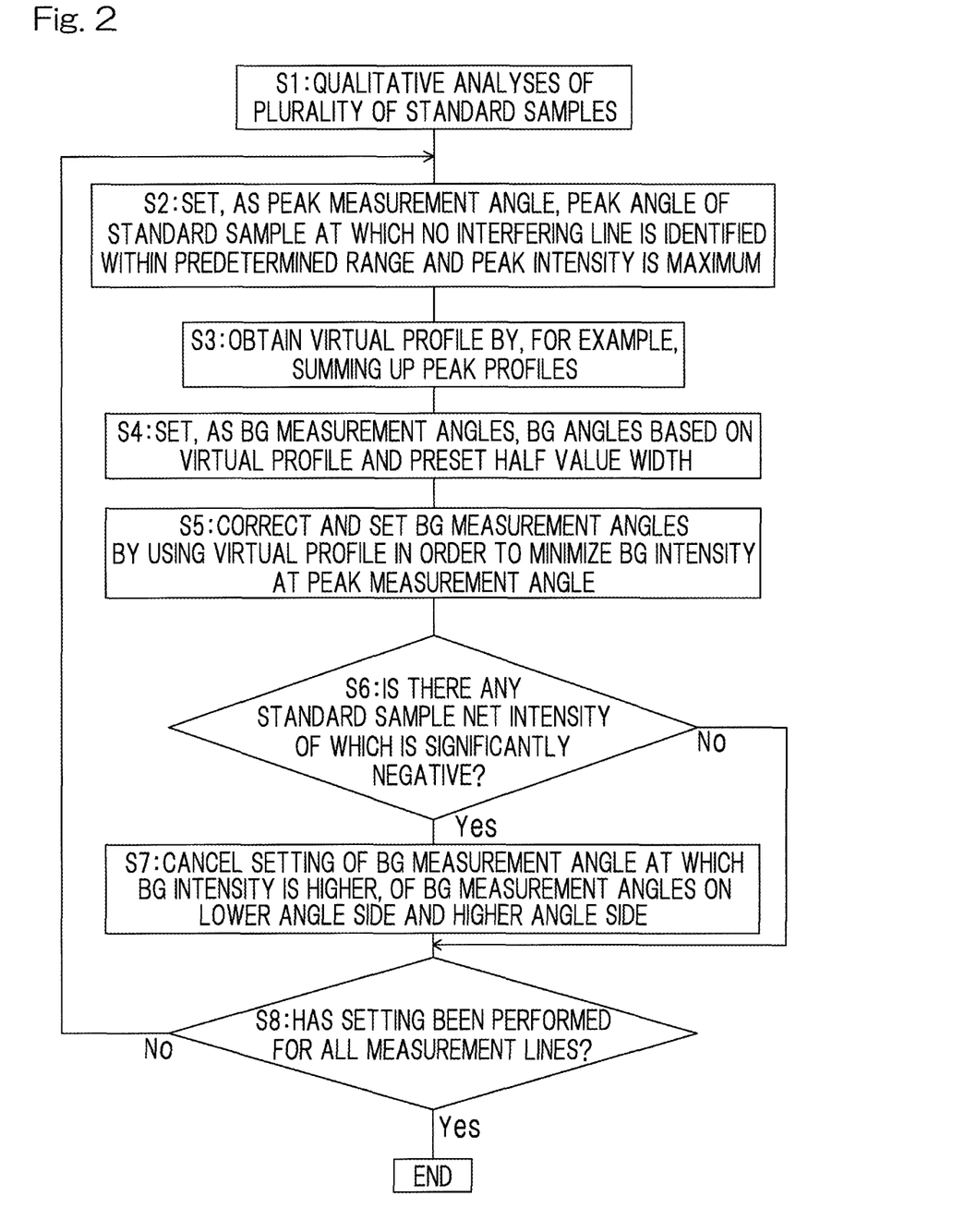
FIG. 2 is a flowchart showing operations of the X-ray fluorescence spectrometer according to the first embodiment.

The quantitative analysis condition setting unit 13 included in the X-ray fluorescence spectrometer according to the first embodiment specifically operates in accordance with the flowchart in FIG. 2. In FIG. 2, etc., "background" is represented as "BG" for simplification. Further, in the quantitative analysis condition setting unit 13, the measurement lines for the analytical samples 1, the half value width of the peak profile of each measurement line, and the sample constituting elements and their contents of each standard sample 14, and the like are preset as the quantitative analysis conditions.

First, at step S1, the qualitative analyses of the plurality of standard samples 14 are performed to obtain, for each of measurement lines identified in each standard sample 14, the peak angle obtained through peak search using parabolic fitting etc., the background angles based on the peak angle and the preset half value width of the peak profile, and the net intensity based on the peak intensity at the peak angle and the background intensities at the background angles. Here, the plurality of standard samples 14 to be subjected to the qualitative analyses preferably include all of the plurality of standard samples 14 for creating one calibration curve corresponding to the analytical samples 1, but only some of the standard samples 14 selected by an operator may be subjected to the qualitative analyses.

The subsequent operations are performed on each of the measurement lines. At step S2, on the basis of the qualitative analysis results, the peak angle of the standard sample 14 at which no interfering line is identified within a predetermined angle range centered on the measurement line and the peak intensity is maximum, is set as a peak measurement angle of the measurement line for the analytical samples 1 in the quantitative analysis conditions. Here, the predetermined angle range centered on the measurement line refers to an angle range which is centered on the peak angle of the measurement line and which is a predetermined number of times (for example, four times) as wide as the preset half value width of the peak profile of the measurement line.

In order to set a sufficiently accurate peak measurement angle of the measurement line, when, in all of the standard samples 14 subjected to the qualitative analyses, the interfering line is identified within the predetermined angle range centered on the measurement line or the net intensity of the measurement line is equal to or lower than a predetermined intensity (including the case where the peak of the measurement line is not detected), the peak angle of the measurement line calculated on the basis of the wavelength of the measurement line and a lattice spacing of the used spectroscopic device is set as the peak measurement angle of the measurement line for the analytical samples 1 in the quantitative analysis conditions.

Figure 3:
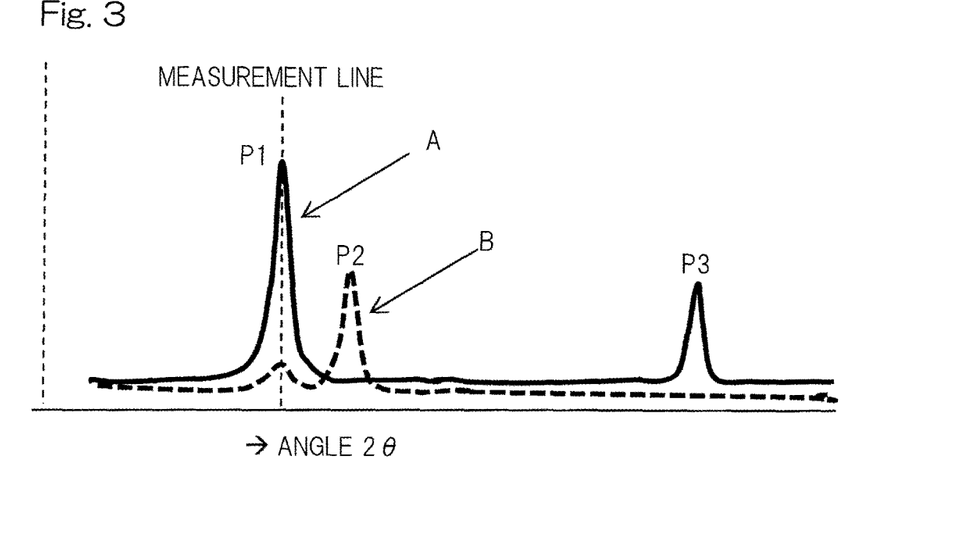
FIG. 3 is a diagram showing the peak profiles of two standard samples in an overlap manner.

Next, at step S3, the peak profiles of the plurality of standard samples 14 subjected to the qualitative analyses are synthesized to obtain the single virtual profile. For example, the peak profiles A, B of two of the standard samples 14, indicated by the solid line and the dashed line in FIG. 3 are summed up to obtain the single virtual profile indicated by the solid line in FIG. 4.

Next, at step S4, on each of the lower angle side and the higher angle side relative to the measurement line, the background angle based on the virtual profile and the preset half value width of the peak profile is set as the background measurement angle of the measurement line for the analytical samples 1 in the quantitative analysis conditions.

Figure 5:
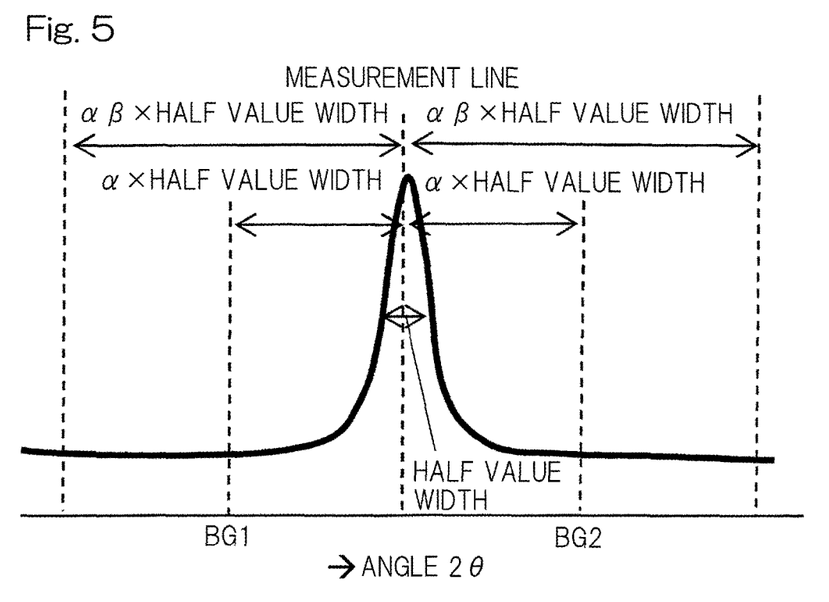
FIG. 5 is a diagram showing a way to obtain a background angle on each of a lower angle side and a higher angle side relative to a measurement line.

Here, a detailed description will be given of a way to obtain the background angle on each of the lower angle side and the higher angle side relative to the measurement line and a way to obtain the net intensity of the measurement line on the basis of the background angles. As shown in FIG. 5, basically, angles, which are each deviated from the peak of the measurement line by a predetermined number of times (represented as "a times", which is four times, for example) of the preset half value width of the peak profile, are used as background angles BG1, BG2, and it is necessary that no interfering line is identified within an angle range which is a constant number of times (represented as "β times", which is two times, for example) as wide as the predetermined number of times of the half value width from the peak of the measurement line. When any interfering line is identified within the angle range the constant number of times as wide as the predetermined number of times of the half value width (that is, αβ times of the half value width, e.g., eight times of the half value width) from the peak of the measurement line, the procedure for obtaining the background angle is repeated with the interfering line regarded as a measurement line.

A background profile is approximated to a straight line connecting two points (at which the background intensities are represented as $I_{BG1}$, $I_{BG2}$, respectively), on a spectrum of the measurement line, at the background angles BG1, BG2 on the lower angle side and the higher angle side relative to the measurement line, respectively. A background intensity at the peak angle is obtained as $k_1 I_{BG1} + k_2 I_{BG2}$ (wherein $k_1$, $k_2$ each represent a background subtraction coefficient, and $k_1 + k_2 = 1$). The background intensity is subtracted from the peak intensity $I_P$ at the peak angle, and thereby, the net intensity $I_{Net}$ of the measurement line is obtained, as shown in the following expression (1). In a case where only one of the background angles on the lower angle side and the higher angle side is adopted as described later, the background subtraction coefficient corresponding to the other non-adopted background angle is set to 0, the spectrum intensity $I_{BG1}$ or $I_{BG2}$ of the measurement line at the adopted background angle directly becomes the background intensity at the peak angle.

$$I_{Net} = I_P - (k_1 I_{BG1} + k_2 I_{BG2}) \quad (1)$$

Figure 4:
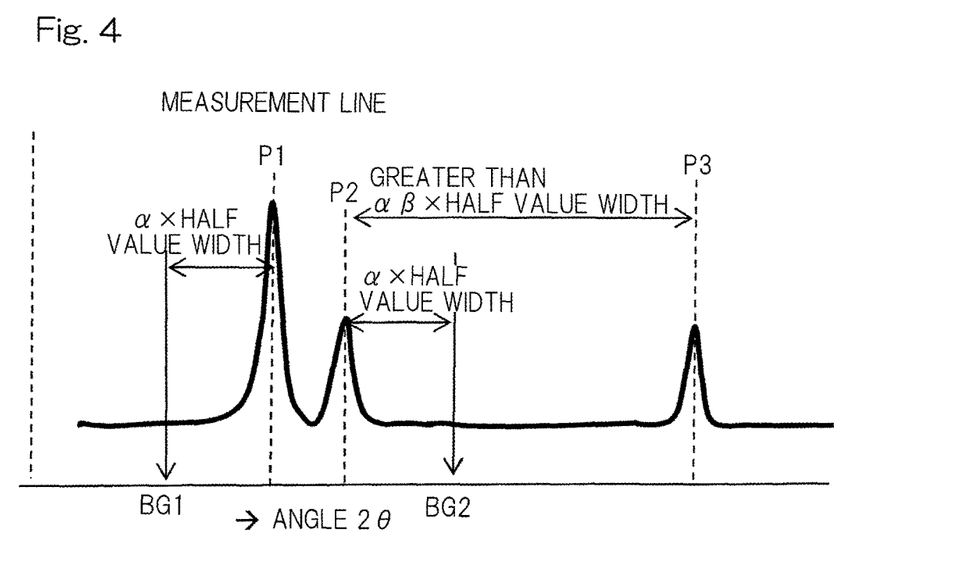
FIG. 4 is a diagram showing a single virtual profile obtained by summing up the two peak profiles in FIG. 3.

On the lower angle side relative to the measurement line in the virtual profile in FIG. 4, no interfering line is identified, and thus, an angle which is far from the peak P1 of the measurement line to the lower angle side by a times of the half value width is set as the background angle BG1. On the higher angle side relative to the measurement line in the virtual profile, the first interfering line having a peak P2 is identified within the angle range, which is αβ times as wide as the half value width from the peak P1 of the measurement line, whereas a peak P3 of the second interfering line which is identified next on the higher angle side falls outside the angle range which is αβ times as wide as the half value width from the peak P2 of the first interfering line. Accordingly, an angle which is far from the peak P2 of the first interfering line by a times of the half value width to the higher angle side is set as the background angle BG2.

In this way, respectively on the lower angle side and the higher angle side relative to the measurement line, the background angles BG1, BG2 obtained on the basis of the virtual profile and the preset half value width of the peak profile are set as the background measurement angle BG1, BG2 of the measurement line for the analytical samples 1 in the quantitative analysis conditions. In the qualitative analyses at step S1, the background angles for each of the measurement lines of each standard sample 14 are obtained on the basis of the corresponding profile and the preset half value width of the peak profile, in the same manner as in the aforementioned description of the virtual profile.

Figure 6:
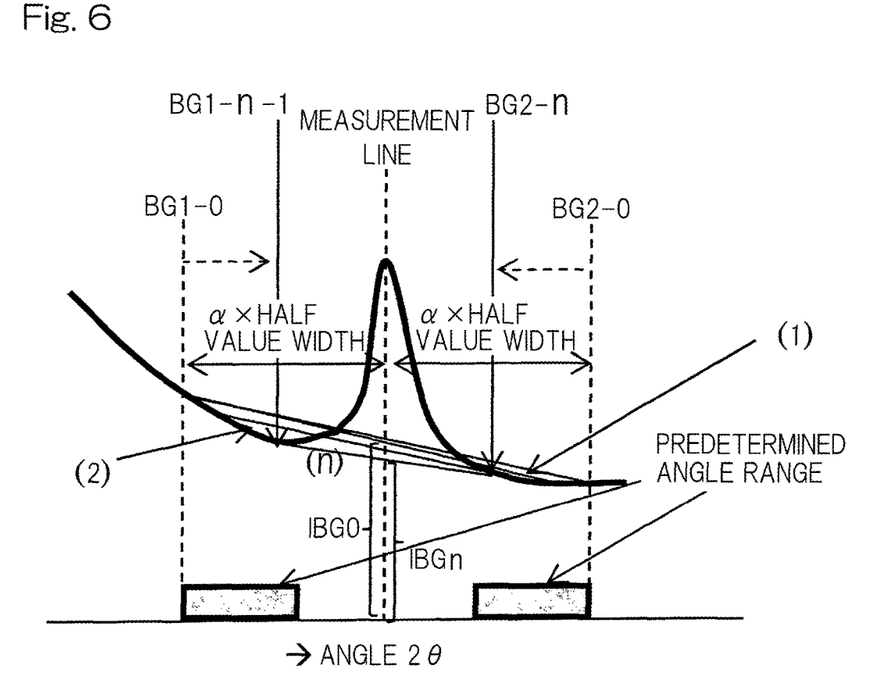
FIG. 6 is a diagram showing a method for correcting and setting background measurement angles of the measurement line by using the virtual profile such that a background intensity at a peak measurement angle of the measurement line is minimized.

Next, at step S5, in the virtual profile shown in FIG. 6, for example, the background measurement angles BG1, BG2 of the measurement line, which have been set on the lower angle side and the higher angle relative to the measurement line at step S4, are set as initial values BG1-0, BG2-0 and alternately moved closer to the measurement line within the predetermined angle range, at the predetermined angle step, starting from, for example, the background measurement angle BG2-0 on the higher angle side. Then, the background measurement angles BG1-$n$-1, BG2-$n$ (or the background measurement angles BG1-$n$, BG2-$n$-1 when n is an even number) which are obtained after the n (odd number)-th movement and by which the background intensity IBGn at the peak measurement angle of the measurement line is minimized, are set as the new background measurement angles BG1, BG2 of the measurement line for the analytical samples 1 in the quantitative analysis conditions.

In FIG. 6, a straight line shown above a straight line indicated as (1) is a straight line connecting two points, on the virtual profile, at the background measurement angles BG1-0, BG2-0 which are the initial values (after 0-th movement). The straight line indicated as (1) is a straight line connecting two points, on the virtual profile, at the background measurement angles BG1-0, BG2-1 after the first movement. Similarly, straight lines indicated as (2), (n) are straight lines connecting two points, on the virtual profile, at the background measurement angles after the second movement and after the n-th movement, respectively. The background intensity at the peak measurement angle of the measurement line after each movement corresponds to an intensity at a point, on the corresponding straight line after the movement, at the peak measurement angle of the measurement line.

Figure 7:
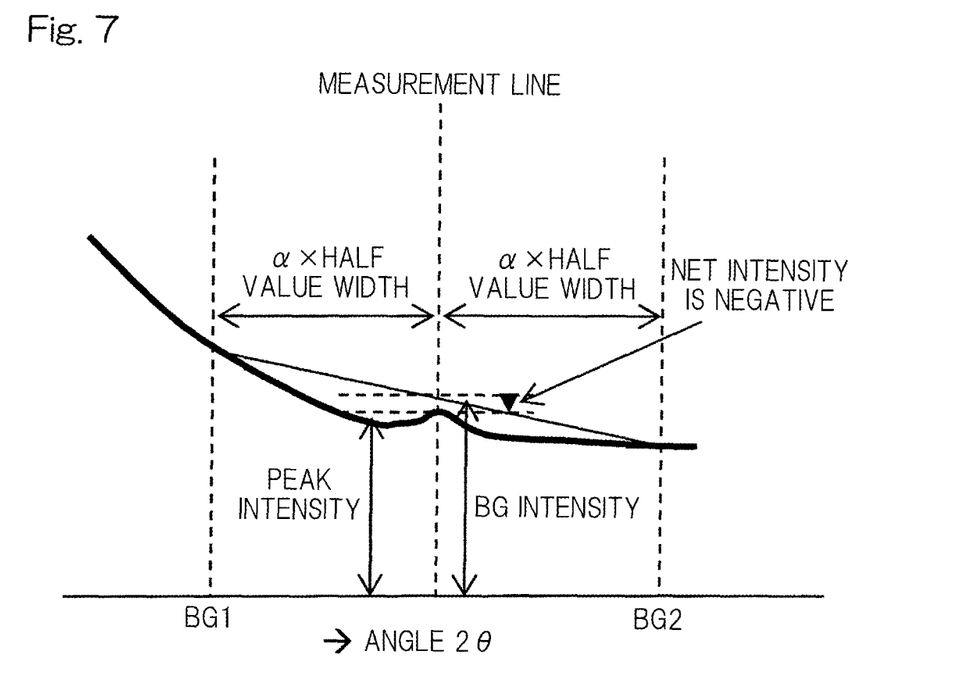
FIG. 7 is a diagram showing an example in which a net intensity of the measurement line is negative.

In a case where the peak of the measurement line appears in a region where the intensity of scattered X-rays of continuous X-rays of the primary X-rays is high, or in a skirt of the peak profile of the interfering line having a high intensity as shown in FIG. 7, if the background measurement angles BG1, BG2 of the measurement line set at step S4 are adopted as they are, the background intensity at the peak measurement angle of the measurement line becomes excessively high and the net intensity of the measurement line becomes negative, so that sufficiently accurate analysis cannot be performed. For this reason, the operation at step S5 is performed to correct and set the background measurement angles BG1, BG2 of the measurement line for the analytical samples 1 in the quantitative analysis conditions so as to appropriately minimize the background intensity IBGn at the peak measurement angle of the measurement line.

More specifically, the background measurement angle, on the lower angle side, of which the initial value is BG1-0 and the background measurement angle, on the higher angle side, of which the initial value is BG2-0 are alternately moved closer to the measurement line, within the the predetermined angle range, at the predetermined angle step. When the background intensity at the peak measurement angle of the measurement line, of which the initial value is set to IBG0 and which decreases each time the background measurement angle is moved, stops decreasing after n+1-th movement, the background measurement angles BG1-$n$-1, BG2-$n$ (or BG1-$n$, BG2-$n$-1) after the last n-th movement are set as the new background measurement angles BG1, BG2 of the measurement line for the analytical samples 1 in the quantitative analysis conditions. As shown in FIG. 6, the predetermined angle ranges are respectively from the initial values BG1-0 and BG2-0 to angles just before a predetermined angle (for example, 1.3 times of the preset half value width of the peak profile of the measurement line) of the peak of the measurement line or the interfering line which the background measurement angle approaching the measurement line first encounters.

As the method for correcting and setting the background measurement angles BG1, BG2 of the measurement line for the analytical samples 1 in the quantitative analysis conditions so as to appropriately minimize the background intensity at the peak measurement angle of the measurement line, the following method may be used instead of the aforementioned method. The same applies for operations of the quantitative analysis condition setting unit 23 included in a spectrometer according to a second embodiment (described later). In this alternative method, in the virtual profile shown in FIG. 6 as an example, the background measurement angles at which intensities each obtained by subtracting the intensity on the virtual profile from the intensity on the straight line connecting two points, on the virtual profile, of the initial values BG1-0, BG2-0 of the background measurement angles become positive and maximum within the predetermined angle ranges on the lower angle side and the higher angle side relative to the measurement line, are set as the new background measurement angles BG1, BG2 of the measurement line for the analytical samples 1 in the quantitative analysis conditions.

Next, at step S6, for each of the plurality of standard samples 14 subjected to the qualitative analyses, the net intensity $I_{Net}$ based on the set background measurement angles BG1, BG2 of the measurement line is obtained through the above expression (1). Then, it is determined whether or not, in at least one of the standard samples 14, the obtained net intensity $I_{Net}$ is negative and the absolute value of the obtained net intensity $I_{Net}$ is greater than the theoretical standard deviation $\sigma_{Net}$ of the net intensity, which is obtained through the following expression (2). When the determination result is No, the flow proceeds to step S8 (described later). When the determination result is Yes, the flow proceeds to step S7. $T_P$, $T_{BG1}$ and $T_{BG2}$ represent measurement times of $I_P$, $I_{BG1}$ and $I_{BG2}$ respectively.

$$\sigma_{Net}=((I_P/T_P+k_1^2 I_{BG1}/T_{BG1}+k_2^2 I_{BG2}/T_{BG2})/1000)^{1/2} \qquad (2)$$

Next, at step S7, setting of the background measurement angle at which the background intensity is higher in the virtual profile, of the background measurement angles BG1, BG2 of the measurement line which are set on the lower angle side and the higher angle side relative to the measurement line, is canceled. For example, in the virtual profile shown in FIG. 6, setting of the background measurement angle BG1 (BG1-$n$-1) at which the background intensity is higher is canceled.

As described above, depending on the state of appearance of the peak of the measurement line, if the background measurement angles BG1, BG2 of the measurement line, which are set at step S4 or corrected and set at step S5, on the lower angle side and the higher angle side relative to the measurement line are adopted as they are, the background intensity at the peak measurement angle of the measurement line becomes excessively high and the net intensity of the measurement line becomes negative, so that sufficiently accurate analysis cannot be performed. For this reason, in such a case, the operations at step S6 and step S7 are performed to correct and set the background measurement angles of the measurement line for the analytical samples 1 in the quantitative analysis conditions such that, of the background measurement angles BG1, BG2 of the measurement line which are set on the lower angle side and the higher angle side relative to the measurement line, only the background measurement angle at which the background intensity is lower in the virtual profile remains.

Next, at step S8, whether or not the background measurement angles have been set for all the measurement lines is determined. When the background measurement angles have not been set for all the measurement lines, the flow returns to step S2. When the background measurement angles have been set for all the measurement lines, the operation is ended.

As described above, the X-ray fluorescence spectrometer according to the first embodiment includes the quantitative analysis condition setting unit 13 that performs the qualitative analyses of the plurality of standard samples 14, that sets the peak angle of the standard sample 14, at which no interfering line is identified within the predetermined angle range centered on the measurement line and the peak intensity is maximum, as a peak measurement angle of the measurement line for the analytical samples 1 in the quantitative analysis conditions, and that obtains the single virtual profile by synthesizing the peak profiles of the plurality of standard samples 14 subjected to the qualitative analyses, and sets background angles based on the virtual profile and the preset half value width of the peak profile, as the background measurement angle of the measurement line for the analytical samples 1 in the quantitative analysis conditions. Accordingly, the qualitative analyses of the plurality of standard samples 14 are automatically performed and the peak measurement angle and the background measurement angles of each measurement line for the analytical samples 1 are automatically set by appropriately reflecting the qualitative analysis results, so that accurate analyses can be performed.

Next, a spectrometer according to the second embodiment of the present invention will be described. The spectrometer according to the second embodiment is different from that according to the first embodiment only in operations of the quantitative analysis condition setting unit 23 provided as a part of the control unit 21, and thus, a description will be given of only the quantitative analysis condition setting unit 23.

The quantitative analysis condition setting unit 23 performs qualitative analyses of the plurality of standard samples 14, to obtain, for each of measurement lines identified in each standard sample 14, a peak angle obtained through peak search, background angles based on the peak angle and the preset half value width of the peak profile, and a net intensity based on a peak intensity at the peak angle and background intensities at the background angles.

On the basis of the qualitative analysis results, the quantitative analysis condition setting unit 23 sets, for each of the measurement lines, the peak angle of the standard sample 14 at which no interfering line is identified within a predetermined angle range centered on the measurement line and the peak intensity is maximum, as a peak measurement angle of the measurement line for the analytical samples 1 in the quantitative analysis conditions. The operations so far are the same as those performed by the quantitative analysis condition setting unit 13 included in the spectrometer according to the first embodiment.

The quantitative analysis condition setting unit 23 further obtains background measurement angle ranges on the basis of the peak profile of the corresponding standard sample 14 and the preset half value width of the peak profile, and sets, on each of the lower angle side and the higher angle side relative to the measurement line, an angle which is closest to the measurement line within the background measurement angle range common to the plurality of standard samples 14 subjected to the qualitative analyses, as a background measurement angle of the measurement line for the analytical samples 1 in the quantitative analysis conditions.

Not necessarily in the X-ray fluorescence spectrometer according to the present invention, but in the X-ray fluorescence spectrometer according to the second embodiment, the quantitative analysis condition setting unit 23 sets, as new background measurement angles of the measurement line for each of the standard samples 14, the background measurement angles by which the background intensity at the peak measurement angle of the measurement line is minimized when, in the peak profile of the corresponding standard sample 14, the background measurement angles of the measurement line which are set on the lower angle side and the higher angle side relative to the measurement line are alternately brought closer to the measurement line within a predetermined angle range, at a predetermined angle step, and sets, on each of the lower angle side and the higher angle side relative to the measurement line, as a new background measurement angle of the measurement line for the analytical samples 1 in the quantitative analysis conditions, the background measurement angle of the measurement line which is farthest from the peak measurement angle of the measurement line, among the new background measurement angles of the measurement lines for the plurality of standard samples 14 subjected to the qualitative analyses.

Figure 8:
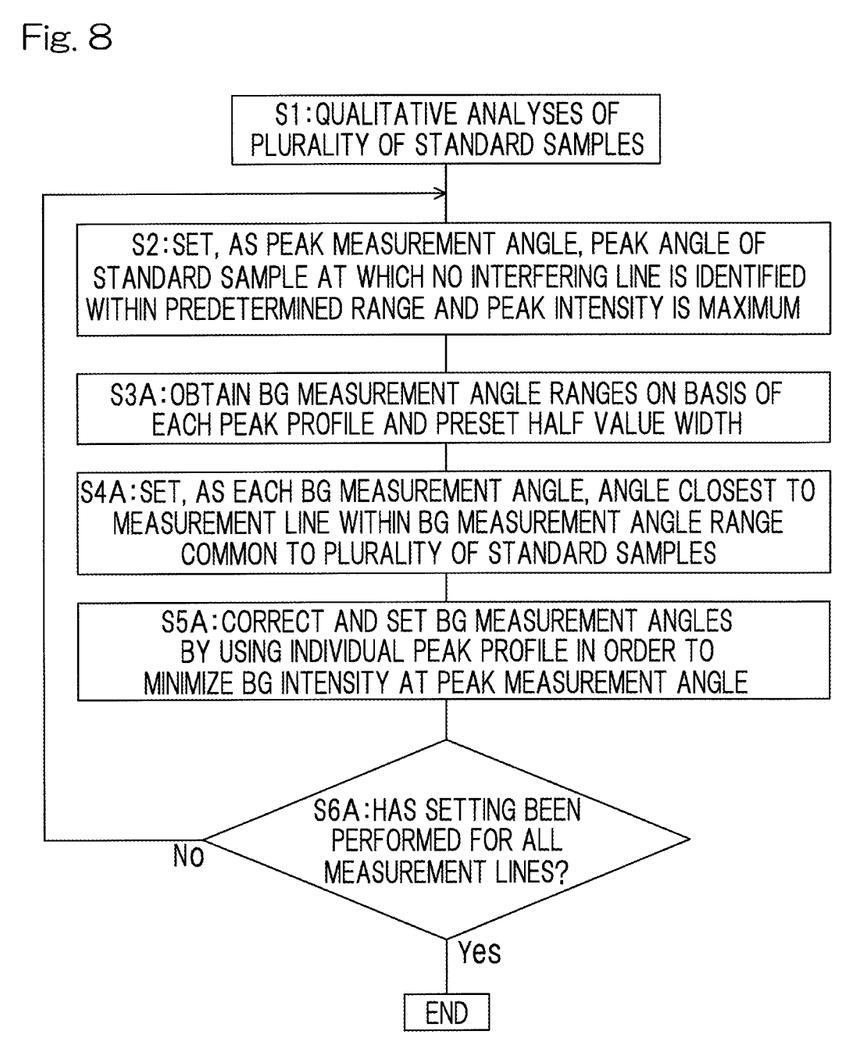
FIG. 8 is a flowchart showing operations of the X-ray fluorescence spectrometer according to the second embodiment.

Specifically, the quantitative analysis condition setting unit 23 included in the X-ray fluorescence spectrometer according to the second embodiment operates in accordance with the flowchart shown in FIG. 8. As in the quantitative analysis condition setting unit 13 included in the spectrometer according to the first embodiment, the measurement line for the analytical samples 1, the half value width of the peak profile of each measurement line, and the sample constituting elements and their contents of each standard sample 14, and the like are preset as the quantitative analysis conditions in the quantitative analysis condition setting unit 23.

The operations at step S1 and step S2 are the same as those performed by the quantitative analysis condition setting unit 13 included in the spectrometer according to the first embodiment. Next, at step S3A, the background measurement angle ranges (angle ranges within which the background measurement angles can be selected) are obtained on the basis of the peak profile of the corresponding standard sample 14 and the preset half value width of the peak profile.

Figure 9:
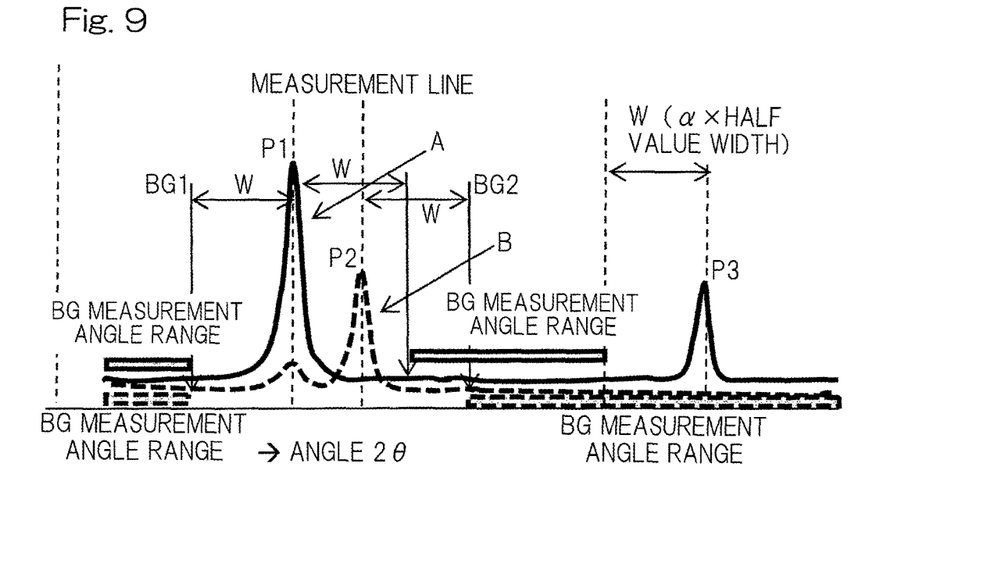
FIG. 9 is a diagram showing a way to obtain background measurement angle ranges on the lower angle side and the higher angle side relative to the measurement line.

For example, in the peak profile A of the standard sample 14 indicated by a solid line in FIG. 9, no interfering line is identified on the lower angle side relative to the measurement line. Thus, a range not exceeding an angle far from the peak P1 of the measurement line by W (a times of the half value width) toward the lower angle side, is set as the background measurement angle range (a rectangular long range indicated by a solid line in FIG. 9). On the higher angle side relative to the measurement line in the peak profile A, the interfering line having the peak P3 is identified beyond an angle range $\alpha\beta$ times as wide as the half value width from the peak P1 of the measurement line. Thus, a range from an angle far from the peak P1 of the measurement line by W (a times of the half value width) toward the higher angle side, to an angle lower than the peak P3 of the interfering line by W (a times of the half value width), is set as the background measurement angle range (a rectangular long range indicated by a solid line in FIG. 9).

In the peak profile B of the standard sample 14 indicated by a dashed line shown in FIG. 9, on the lower angle side relative to the measurement line, no interfering line is identified. Thus, a range not exceeding an angle far from the peak P1 of the measurement line by W (a times of the half value width) toward the lower angle side, is set as the background measurement angle range (a rectangular long range indicated by a dashed line in FIG. 9). On the higher angle side relative to the measurement line in the peak profile B, the interfering line having the peak P2 is identified within an angle range $\alpha\beta$ times as wide as the half value width from the peak P1 of the measurement line. Thus, a range not below an angle far from the peak P2 of the interfering line by W (a times of the half value width) toward the higher angle side, is set as the background measurement angle range (a rectangular long range indicated by a dashed line in FIG. 9).

Next, at step S4A, an angle, which is closest to the measurement line within the background measurement angle range common to the plurality of standard samples 14 subjected to the qualitative analyses, on each of the lower angle side and the higher angle side relative to the measurement line, are set as the background measurement angle of the measurement line for the analytical samples 1 in the quantitative analysis conditions. For example, in the case of the two standard samples 14 for which the peak profiles A, B are shown in FIG. 9, the angles BG1, BG2, each of which is closest to the measurement line within the background measurement angle range common to the two standard samples 14, on respectively the lower angle side and the higher angle side relative to the measurement line, are set as the background measurement angles BG1, BG2 of the measurement line for the analytical samples 1 in the quantitative analysis conditions.

Next, at step S5A, in each of the peak profile of the corresponding standard sample 14, the background measurement angles BG1, BG2 of the measurement line set on the lower angle side and the higher angle side relative to the measurement line are set as the initial values BG1-0, BG2-0, and are alternately brought closer to the measurement line within the predetermined angle range, at the predetermined angle step. Then, the background measurement angles by which the background intensity at the peak measurement angle of the measurement line is minimized are set as the new background measurement angles of the measurement line for the corresponding standard sample 14. That is, the operation, which is performed on the virtual profile at step S5 by the quantitative analysis condition setting unit 13 included in the spectrometer according to the first embodiment, is performed on the peak profile of the corresponding standard sample 14, and then, the background measurement angles by which the background intensity at the peak measurement angle of the measurement line is minimized are set as the new background measurement angles of the measurement line for the corresponding standard sample 14.

Figure 10:
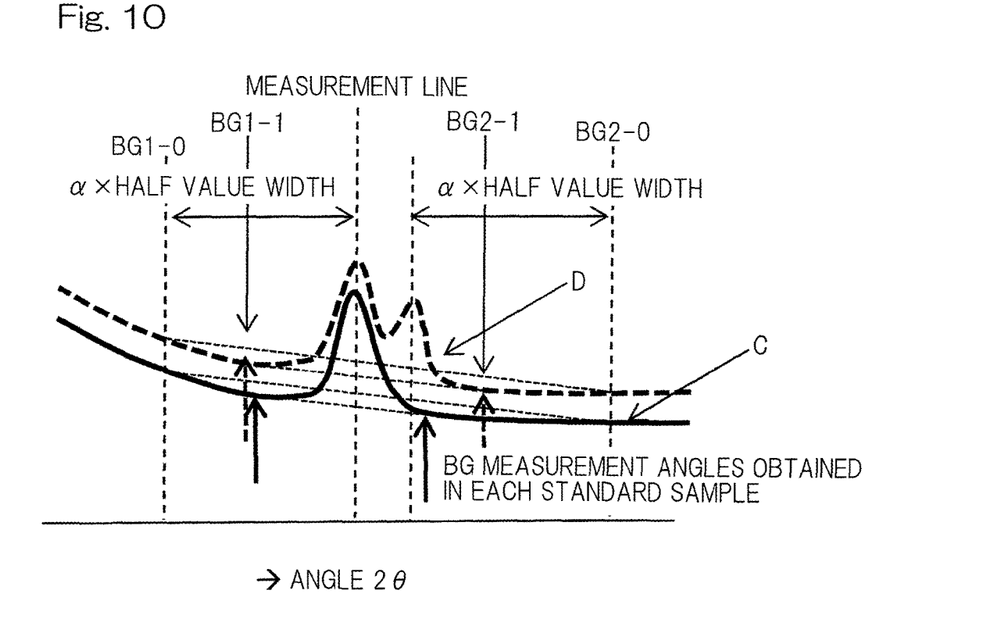
FIG. 10 is a diagram showing a method for correcting and setting the background measurement angles of the measurement line by using a peak profile of each standard sample such that the background intensity at the peak measurement angle of the measurement lines is minimized.

For example, in the case of the peak profile C of the standard sample 14 indicated by a solid line in FIG. 10, on the lower angle side relative to the measurement line, the background measurement angle is shifted from the initial value BG1-0 to the new background measurement angle indicated by a solid-line upward arrow, which is closer to the measurement line than the initial value BG1-0. On the higher angle side relative to the measurement line, the background measurement angle is shifted from the initial value BG2-0 to the new background measurement angle indicated by a solid-line upward arrow, which is closer to the measurement line than the initial value BG2-0. In the case of the peak profile D of the standard sample 14 indicated by a dashed line in FIG. 10, on the lower angle side relative to the measurement line, the background measurement angle is shifted from the initial value BG1-0 to the new background measurement angle indicated by a dashed-line upward arrow, which is closer to the measurement line than the initial value BG1-0. On the higher angle side relative to the measurement line, the background measurement angle is shifted from the initial value BG2-0 to the new background measurement angle indicated by a dashed-line upward arrow, which is closer to the measurement line than the initial value BG2-0.

On each of the lower angle side and the higher angle side relative to the measurement line, among the new background measurement angles of the measurement line for the plurality of standard samples 14 subjected to the qualitative analyses, the background measurement angle of the measurement line which is farthest from the peak measurement angle of the measurement line is set as the new background measurement angle BG1, BG2 of the measurement line for the analytical samples 1 in the quantitative analysis conditions.

For example, in the case of the two standard samples 14 for which the peak profiles C, D are shown in FIG. 10, among the new background measurement angles (background measurement angles indicated by solid- and dashed-line upward arrows) of the measurement line for the two standard samples 14, background measurement angles of the measurement line each farthest from the peak measurement angle of the measurement line, that is, the background measurement angles BG1-1, BG2-1 indicated by the dashed-line upward arrows on respectively the lower angle side and the higher angle side relative to the measurement line, are set as the new background measurement angles BG1, BG2 of the measurement line for the analytical samples 1 in the quantitative analysis conditions.

As described above, depending on the state of appearance of the peak of the measurement line, if the background measurement angles BG1, BG2 of the measurement line set at step S4A are adopted as they are, the background intensity at the peak measurement angle of the measurement line becomes excessively high and the net intensity of the measurement line becomes negative, so that sufficiently accurate analysis cannot be performed. For this reason, the operation at step S5A is performed to correct and set the background measurement angles BG1, BG2 of the measurement line for the analytical samples 1 in the quantitative analysis conditions so as to appropriately minimize the background intensity at the peak measurement angle of the measurement line.

Next, at step S6A, whether or not the background measurement angles have been set for all the measurement lines is determined. When the background measurement angles have not been set for all the measurement lines, the flow returns to step S2. When the background measurement angles have been set for all the measurement lines, the operation is ended.

As described above, the X-ray fluorescence spectrometer according to the second embodiment includes the quantitative analysis condition setting unit 23 that performs the qualitative analyses of the plurality of standard samples 14, and sets, as the peak measurement angle of the measurement line for the analytical samples 1 in the quantitative analysis conditions, the peak angle of the standard sample 14 at which no interfering line is identified within the predetermined angle range centered on the measurement line and the peak intensity is maximum, and that obtains the background measurement angle ranges on the basis of the peak profile of the corresponding standard sample 14 and the preset half value width of the peak profile and sets, as each background measurement angle of the measurement line for the analytical samples 1 in the quantitative analysis conditions, each angle closest to the measurement line within the background measurement angle range which is common to the plurality of standard samples 14 subjected to the qualitative analyses. Accordingly, as in the spectrometer according to the first embodiment, the qualitative analyses of the plurality of standard samples 14 are automatically performed and the peak measurement angle and the background measurement angles of each measurement line for the analytical samples 1 are automatically set by appropriately reflecting the qualitative analysis results, so that accurate analyses can be performed.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are to be construed as included therein.

REFERENCE NUMERALS

1 . . . analytical sample
3 . . . primary X-rays
5 . . . secondary X-rays
13, 23 . . . quantitative analysis condition setting unit
14 . . . standard sample

What is claimed is:
1. A sequential X-ray fluorescence spectrometer which irradiates a sample with primary X-rays and measures the intensities of generated secondary X-rays, the spectrometer comprising:
   a plurality of standard samples to create calibration curves corresponding to analytical samples; and a quantitative analysis condition setting unit configured to preset, as quantitative analysis conditions, with measurement lines for the analytical samples, a half value width of a peak profile of each measurement line, sample constituting elements and their contents of each standard sample, wherein the quantitative analysis condition setting unit performs qualitative analyses of the plurality of standard samples, to obtain, for each of measurement lines identified in each standard sample, a peak angle obtained through peak search, background angles based on the peak angle and the preset half value width of the peak profile, and a net intensity based on a peak intensity at the peak angle and background intensities at the background angles, sets, for each of the measurement lines, the peak angle of the standard sample at which no interfering line is identified within a predetermined angle range centered on the measurement line and the peak intensity is maximum, as a peak measurement angle of the measurement line for the analytical samples in the quantitative analysis conditions, and obtains, for each of the measurement lines, a single virtual profile by synthesizing peak profiles of the plurality of standard samples subjected to the qualitative analyses, and sets the background angle on each of a lower angle side and a higher angle side relative to the measurement line, as a background measurement angle of the measurement line for the analytical samples in the quantitative analysis conditions, the background angles being based on the virtual profile and the preset half value width of the peak profile.

2. The X-ray fluorescence spectrometer as claimed in claim 1, wherein the quantitative analysis condition setting unit sets, as new background measurement angles of the measurement line for the analytical samples in the quantitative analysis conditions, the background measurement angles by which the background intensity at the peak measurement angle of the measurement line is minimized when, in the virtual profile, the background measurement angles of the measurement line which are set on the lower angle side and the higher angle side relative to the measurement line are alternately brought closer to the measurement line within a predetermined angle range, at a predetermined angle step.

3. The X-ray fluorescence spectrometer as claimed in claim 1, wherein the quantitative analysis condition setting unit obtains, for each of the measurement lines, a net intensity based on the set background measurement angles of the measurement line for each of the plurality of standard samples subjected to the qualitative analyses, and when, in at least one of the standard samples, the obtained net intensity is negative and the absolute value of the obtained net intensity is greater than a theoretical standard deviation of the net intensity, the quantitative analysis condition setting unit cancels setting of the background measurement angle at which the background intensity is higher in the virtual profile, of the background measurement angles of the measurement line which are set on the lower angle side and the higher angle side relative to the measurement line.

4. A sequential X-ray fluorescence spectrometer which irradiates a sample with primary X-rays and measures the intensities of generated secondary X-rays, the spectrometer comprising:

a plurality of standard samples to create calibration curves corresponding to analytical samples; and a quantitative analysis condition setting unit configured to preset, as quantitative analysis conditions, with measurement lines for the analytical samples, a half value width of a peak profile of each measurement line, sample constituting elements and their contents of each standard sample, wherein the quantitative analysis condition setting unit performs qualitative analyses of the plurality of standard samples, to obtain, for each of measurement lines identified in each standard sample, a peak angle obtained through peak search, background angles based on the peak angle and the preset half value width of the peak profile, and a net intensity based on a peak intensity at the peak angle and background intensities at the background angles, sets, for each of the measurement lines, the peak angle of the standard sample at which no interfering line is identified within a predetermined angle range centered on the measurement line and the peak intensity is maximum, as a peak measurement angle of the measurement line for the analytical samples in the quantitative analysis conditions, and obtains, for each of the measurement lines, background measurement angle ranges on the basis of the peak profile of the corresponding standard sample and the preset half value width of the peak profile, and sets an angle, which is closest to the measurement line within the background measurement angle range, on each of a lower angle side and a higher angle side relative to the measurement line, as a background measurement angle of the measurement line for the analytical samples in the quantitative analysis conditions, the background measurement angle range being common to the plurality of standard samples subjected to the qualitative analyses.

5. The X-ray fluorescence spectrometer as claimed in claim 4, wherein the quantitative analysis condition setting unit sets, as new background measurement angles of the measurement line for each of the standard samples, the background measurement angles by which the background intensity at the peak measurement angle of the measurement line is minimized when, in the peak profile of the corresponding standard sample, the background measurement angles of the measurement line which are set on the lower angle side and the higher angle side relative to the measurement line are alternately brought closer to the measurement line within a predetermined angle range, at a predetermined angle step, and sets, on each of the lower angle side and the higher angle side relative to the measurement line, as a new background measurement angle of the measurement line for the analytical samples in the quantitative analysis conditions, the background measurement angle of the measurement line which is farthest from the peak measurement angle of the measurement line, among the new background measurement angles of the measurement line for the plurality of standard samples subjected to the qualitative analyses.

* * * * *